United States Patent
Xue et al.

(10) Patent No.: US 6,972,174 B2
(45) Date of Patent: Dec. 6, 2005

(54) METHOD FOR DETECTING SINGLE NUCLEOTIDE POLYMORPHISMS (SNP'S) AND POINT MUTATIONS

(75) Inventors: Hong Xue, New Territories (HK); Jeffrey Tze-Fei Wong, Mid-Levels (HK)

(73) Assignee: PharmacoGenetics, Ltd., Hong Kong (CN)

( * ) Notice: Subject to any disclaimer, the term of this patent is extended or adjusted under 35 U.S.C. 154(b) by 589 days.

(21) Appl. No.: 10/162,530

(22) Filed: Jun. 4, 2002

(65) Prior Publication Data

US 2003/0017487 A1    Jan. 23, 2003

Related U.S. Application Data

(63) Continuation-in-part of application No. 09/876,727, filed on Jun. 6, 2001, now abandoned.

(51) Int. Cl.[7] .......................... C12Q 1/68; C12P 19/34; C07H 21/02
(52) U.S. Cl. .......................... 435/6; 435/91.2; 536/23.1
(58) Field of Search .................. 435/6, 91.2; 536/23.1

(56) References Cited

U.S. PATENT DOCUMENTS 6,110,709 A      8/2000  Ausubel et al.
6,479,242 B1 *  11/2002  Guo et al. ..................... 435/6

FOREIGN PATENT DOCUMENTS

WO      WO 93/02212 A1    2/1993
WO      WO 00/20853 A1    4/2000

OTHER PUBLICATIONS

Sun et al (Nucleic Acids Research (Jun. 15, 2000) 28(12): e68, p. i-viii).*
Okano et al (Sensors and Actuators B (2000) 64:88-94.*
Piggee et al (J. Chromatog. A (1997) 781:367-375.*
J. Sambrook, et al., Molecular Cloning A Laboratory Manual, Second Edition, 1989, pp. 13.65-13.69, Cold Spring Harbor Laboratory Press.
Ausubel, et al., Current Protocols in Molecular Biology, 1998, pp. 7.4A. 13-7.4A. 19, vol. 1, John Wiley & Sons.

* cited by examiner

*Primary Examiner*—Jeffrey Fredman
(74) *Attorney, Agent, or Firm*—Jackson Walker L.L.P.

(57) ABSTRACT

A method of genotyping single nucleotide polymorphisms ("SNP") and point mutations in nucleic acid based on chain extension by polymerase. This invention is based on the fact that the nucleoside immediately 5' adjacent to any SNP/point mutation site is known, and the neighboring sequence immediately 3' adjacent to the site is also known. A primer complementary to the sequence directly adjacent to the SNP on the 3' side in a target polynucleotide is used for chain elongation. The polymerase reaction mixture contains one chain-terminating nucleotide having a base complementary to the nucleotide directly adjacent to the SNP on the 5' side in the target polynucleotide. An additional dNTP may be added to produce a primer with the maximum of a two-base extension. The resultant elongation/termination reaction products are analyzed for the length of chain extension of the primer, or for the amount of label incorporation from a labeled form of the terminator nucleotide.

83 Claims, 12 Drawing Sheets

| Reaction Mixture | A-Mix: dATP ddCTP Primer Target DNA | T-Mix: dTTP ddCTP Primer Target DNA | G-Mix: dGTP ddCTP Primer Target DNA | Control-Mix: ddCTP Primer Target DNA | Sequence Around Haploid SNP |
|---|---|---|---|---|---|
| Number of bases extended from primer and sequences of the extended products | 0 base | 2 bases 3'dCTAAXXX5' | 0 base | 0 base | CG[A]TT |
| | 2 bases 3'dCAAAXXX5' | 0 base | 0 base | 0 base | CG[T]TT |
| | 0 base | 0 base | 2 bases 3'dCGAAXXX5' | 0 base | CG[C]TT |
| | 1 base 3'dCAAXXX5' | 1 base 3'dCAAXXX5' | 1 base 3'dCAAXXX5' | 1 base 3'dCAAXXX5' | CG[G]TT |

Fig. 2

| Reaction Mixture | A-Mix: dATP ddCTP Primer Target DNA | T-Mix: dTTP ddCTP Primer Target DNA | G-Mix: dGTP ddCTP Primer Target DNA | Control-Mix: ddCTP Primer Target DNA | Sequence Around Diploid SNP |
|---|---|---|---|---|---|
| Number of bases extended from primer and sequences of the extended products | 0 base | 2 bases 3'dCTAAXXX5' | 0 base | 0 base | Homozygous: CGATT / CGATT |
| | 2 bases 3'dCAAAXXX5' | 0 base | 0 base | 0 base | CGTTT / CGTTT |
| | 0 base | 0 base | 2 bases 3'dGAAXXX5' | 0 base | CGCTT / CGCTT |
| | 1 base 3'dCAAXXX5' | 1 base 3'dCAAXXX5' | 1 base 3'dCAAXXX5' | 1 base 3'dCAAXXX5' | CGGTT / CGGTT |
| | 2 bases 3'dCAAAXXX5' | 2 bases 3'dCTAAXXX5' | 0 base | 0 base | Heterozygous: CGATT / CGTTT |
| | 0 base | 0 base | 2 bases 3'dGAAXXX5' | 0 base | CGATT / CGGTT (note: see figure) |
| | 1 base 3'dCAAXXX5' | 1 base 3'dCAAXXX5' | 1 base 3'dCAAXXX5' | 1 base 3'dCAAXXX5' | CGATT / CGCTT |
| | 2 bases 3'dCAAAXXX5' | 2 bases 3'dCTAAXXX5' 1 base 3'dCAAXXX5' | 1 base 3'dCAAXXX5' | 0 base | CGTTT / CGGTT |
| | 2 bases 3'dCAAAXXX5' 1 base 3'dCAAXXX5' | 1 base 3'dCAAXXX5' | 2 bases 3'dGAAXXX5' 1 base 3'dCAAXXX5' | 1 base 3'dCAAXXX5' | CGTTT / CGCTT |
| | 1 base 3'dCAAXXX5' | 1 base 3'dCAAXXX5' | 2 bases 3'dGAAXXX5' 1 base 3'dCAAXXX5' | 1 base 3'dCAAXXX5' | CGGTT / CGCTT |

Fig. 3

| Reaction Mixture | A-Mix:<br>dATP<br>ddCTP<br>Primer<br>Target DNA | T-Mix:<br>dTTP<br>ddCTP<br>Primer<br>Target DNA | G-Mix:<br>dGTP<br>ddCTP<br>Primer<br>Target DNA | Control-Mix:<br>ddCTP<br>Primer<br>Target DNA | Sequence Around Haploid SNP |
|---|---|---|---|---|---|
| Amount of label incorporated from labelled dideoxyribonucleotide (regardless of actual length of primer elongation) | 0 | 2x | 0 | 0 | CG[A]TT |
| | 2x | 0 | 0 | 0 | CG[T]TT |
| | 0 | 0 | 2x | 0 | CG[C]TT |
| | 2x | 2x | 2x | 2x | CG[G]TT |

Fig. 4

| Reaction Mixture | A-Mix: dATP ddCTP Primer Target DNA | T-Mix: dTTP ddCTP Primer Target DNA | G-Mix: dGTP ddCTP Primer Target DNA | Control-Mix: ddCTP Primer Target DNA | Sequence Around Diploid SNP | |
|---|---|---|---|---|---|---|
| Amount of label incorporated from labeled dideoxyribonucleotide (regardless of actual length of primer elongation) | | | | | | Homozygous |
| | 0 | 2x | 0 | 0 | CGATT / CGATT | |
| | 2x | 0 | 0 | 0 | CGTTT / CGTTT | |
| | 0 | 0 | 2x | 0 | CGCTT / CGCTT | |
| | 2x | 2x | 2x | 2x | CGGTT / CGGTT | |
| | | | | | | Heterozygous |
| | 1x | 1x | 0 | 0 | CGATT / CGTTT | |
| | 0 | 2x | 1x | 0 | CGATT / CGCTT | |
| | 1x | 0 | 1x | 1x | CGATT / CGGTT | |
| | 1x | 1x | 1x | 0 | CGTTT / CGCTT | |
| | 2x | 1x | 1x | 1x | CGTTT / CGGTT | |
| | 1x | 1x | 2x | 1x | CGCTT / CGGTT | |

Fig. 5

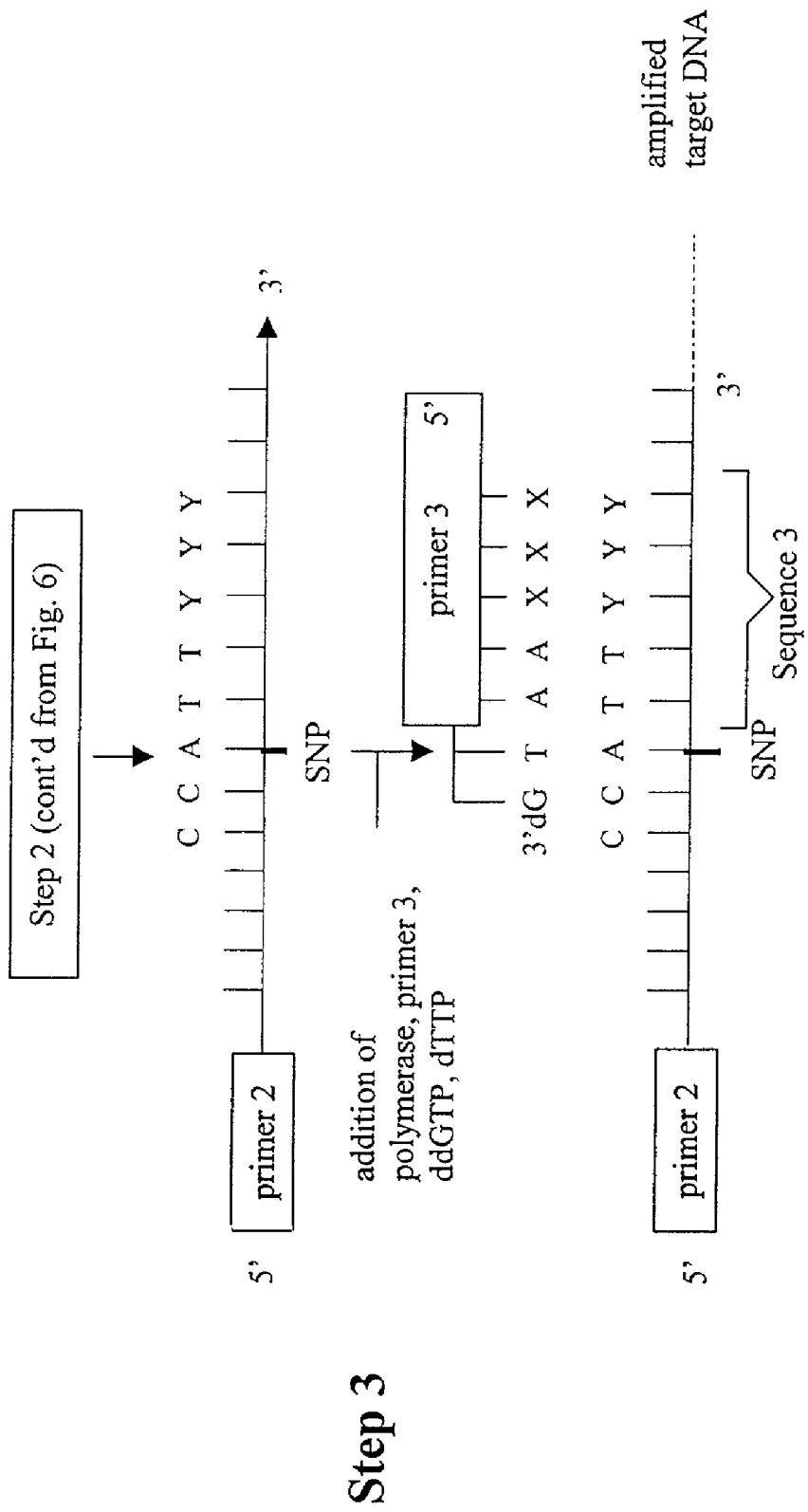

| Reaction Mixture | A-Mix: dATP ddGTP Primer 3 Target DNA | T-Mix: dTTP ddGTP Primer 3 Target DNA | C-Mix: dCTP ddGTP Primer 3 Target DNA | Control-Mix: ddGTP Primer 3 Target DNA | Sequence Around Haploid SNP |
|---|---|---|---|---|---|
| Number of bases extended from primer and sequences of the extended products | 0 base | 2 bases 3'dGTAAXXX5' | 0 base | 0 base | CC[A]TT |
| | 2 bases 3'dGAAAXXX5' | 0 base | 0 base | 0 base | CC[T]TT |
| | 0 base | 0 base | 2 bases 3'dGCAAXXX5' | 0 base | CC[G]TT |
| | 1 base 3'dGAAXXX5' | 1 base 3'dGAAXXX5' | 1 base 3'dGAAXXX5' | 1 base 3'dGAAXXX5' | CC[C]TT |

Fig. 8

| Reaction Mixture | A-Mix: dATP ddGTP Primer 3 Target DNA | T-Mix: dTTP ddGTP Primer 3 Target DNA | C-Mix: dCTP ddGTP Primer 3 Target DNA | Control-Mix: ddGTP Primer 3 Target DNA | Sequence Around Diploid SNP |
|---|---|---|---|---|---|
| | | | | | Homozygous |
| | 0 base | 2 bases 3'dGTAAXXX5' | 0 base | 0 base | CCATT CCATT |
| | 2 bases 3'dGAAAXXX5' | 0 base | 0 base | 0 base | CCTTT CCTTT |
| | 0 base | 0 base | 2 bases 3'dGCAAXXX5' | 0 base | CCGTT CCGTT |
| | 1 base 3'dGAAXXX5' | 1 base 3'dGAAXXX5' | 1 base 3'dGAAXXX5' | 1 base 3'dGAAXXX5' | CCATT CCGTT |
| | | | | | Heterozygous |
| | 2 bases 3'dGAAAXXX5' | 2 bases 3'dGTAAXXX5' | 1 base 3'dGAAXXX5' | 0 base | CCATT CCTTT |
| | 1 base 3'dGAAXXX5' | 2 bases 3'dGTAAXXX5' | 2 bases 3'dGCAAXXX5' | 1 base 3'dGAAXXX5' | CCATT CCGTT |
| | 0 base | 1 base 3'dGAAXXX5' | 1 base 3'dGAAXXX5' | 0 base | CCTTT CCATT |
| | 1 base 3'dGAAXXX5' | 1 base 3'dGAAXXX5' | 2 bases 3'dGCAAXXX5' | 1 base 3'dGAAXXX5' | CCTTT CCGTT |
| | 2 bases 3'dGAAAXXX5' | 0 base | 2 bases 3'dGCAAXXX5' | 0 base | CCGTT CCATT |
| | 1 base 3'dGAAXXX5' | 1 base 3'dGAAXXX5' | 2 bases 3'dGCAAXXX5' 1 base 3'dGAAXXX5' | 1 base 3'dGAAXXX5' | CCGTT CCGTT |

Number of bases extended from primer and sequences of the extended products

Fig. 9

| Reaction Mixture | A-Mix:<br>dATP<br>ddGTP<br>Primer 3<br>Target DNA | T-Mix:<br>dTTP<br>ddGTP<br>Primer 3<br>Target DNA | C-Mix:<br>dCTP<br>ddGTP<br>Primer 3<br>Target DNA | Control-Mix:<br>ddGTP<br>Primer 3<br>Target DNA | Sequence Around Haploid SNP |
|---|---|---|---|---|---|
| Amount of label incorporated from labeled dideoxyribonucleotide (regardless of actual length of primer elongation) | 0 | 2x | 0 | 0 | CC[A]TT |
| | 2x | 0 | 0 | 0 | CC[T]TT |
| | 0 | 0 | 2x | 0 | CC[G]TT |
| | 2x | 2x | 2x | 2x | CC[G]TT |

| Reaction Mixture | A-Mix: dATP ddGTP Primer 3 Target DNA | T-Mix: dTTP ddGTP Primer 3 Target DNA | C-Mix: dCTP ddGTP Primer 3 Target DNA | Control-Mix: ddGTP Primer 3 Target DNA | Sequence Around Diploid SNP |
|---|---|---|---|---|---|
| *Amount of label incorporated from labeled dideoxyribonucleotide (regardless of actual length of primer elongation)* | | | | | |
| Homozygous | | | | | |
| | 0 | 2x | 0 | 0 | ccATT / ccATT |
| | 2x | 0 | 0 | 0 | ccTTT / ccTTT |
| | 0 | 0 | 2x | 0 | ccGTT / ccGTT |
| | 2x | 2x | 2x | 2x | ccGTT / ccGTT |
| Heterozygous | | | | | |
| | 1x | 1x | 0 | 0 | ccATT / ccTTT |
| | 0 | 2x | 1x | 1x | ccATT / ccGTT |
| | 2x | 1x | 1x | 0 | ccATT / ccGTT |
| | 1x | 0 | 1x | 1x | ccTTT / ccGTT |
| | 1x | 1x | 2x | 0 | ccGTT / ccGTT |
| | 1x | 1x | 2x | 1x | ccGTT / ccGTT |

| Reaction Mixture | Reaction 1 ddGTP Primer Target DNA | Reaction 2: Main Incubation | | | | Sequence Around SNP | Ploidy |
| --- | --- | --- | --- | --- | --- | --- | --- |
| | | A-Mix: dATP ddGTP Primer Target DNA | T-Mix: dTTP ddGTP Primer Target DNA | C-Mix: dCTP ddGTP Primer Target DNA | Control-Mix ddGTP Primer Target DNA | | |
| | 0 | 0 | 2x | 0 | 0 | CCATT | Haploid |
| | 0 | 2x | 0 | 0 | 0 | CCTTT | Haploid |
| | 0 | 0 | 0 | 2x | 0 | CCGTT | Haploid |
| | 2x | 0 | 0 | 0 | 0 | CCCTT | Haploid |
| | 0 | 0 | 2x | 0 | 0 | CCATT | Diploid Homozygous |
| | 0 | 2x | 0 | 0 | 0 | CCTTT | Diploid Homozygous |
| | 0 | 0 | 0 | 2x | 0 | CCGTT | Diploid Homozygous |
| | 2x | 0 | 0 | 0 | 0 | CCCTT | Diploid Homozygous |
| | 0 | 1x | 1x | 0 | 0 | CCATT / CCTTT | Diploid Heterozygous |
| | 0 | 0 | 1x | 1x | 0 | CCATT / CCGTT | Diploid Heterozygous |
| | 1x | 0 | 1x | 0 | 0 | CCATT / CCCTT | Diploid Heterozygous |
| | 0 | 1x | 0 | 1x | 0 | CCTTT / CCGTT | Diploid Heterozygous |
| | 1x | 1x | 0 | 0 | 0 | CCTTT / CCCTT | Diploid Heterozygous |
| | 1x | 0 | 0 | 1x | 0 | CCGTT / CCCTT | Diploid Heterozygous |

Amount of label incorporated from labeled dideoxyribonucleotide (regardless of actual length of primer elongation)

Fig. 12

METHOD FOR DETECTING SINGLE NUCLEOTIDE POLYMORPHISMS (SNP'S) AND POINT MUTATIONS

This is a continuation-in-part of application, Ser. No. 09/876,727, filed on Jun. 6, 2001 abandoned, the entire content of which is hereby incorporated by reference.

BACKGROUND

The present invention relates to a method of identifying or genotyping single nucleotide polymorphisms ("SNP") and point mutations in a nucleic acid molecule. This method utilizes a null, single or double base extension of an oligonucleotide primer to identify an SNP. The oligonucleotide primer is complementary to the nucleic acid molecule that contains the SNP or point mutation. The predicted extension length of the oligonucleotide primer is compared with the experimental extension lengths or amounts of isotope labeled incorporation of the extended nucleotides to identify the SNP or point mutation.

The human genome has been sequenced and the future efforts in genetics will be compare the sequences of different individuals in order to understand human diseases. It is believed that there is about one polymorphism per 1,000 bases, which makes single nucleotide polymorphisms ("SNP") and point mutations the most abundant type of genetic variations. Thus, the high density of SNP and point mutations in genomes make them powerful tools for mapping and diagnosing disease-related alleles. Although it appears that most SNP's and point mutations occur in non-coding regions, primarily between genes, many SNP's and point mutations occur in exons and introns.

The SNP's and point mutations have a number of properties of interest. Since SNP's and point mutations are inherited, such aberrant sequences can be used to determine genetic defects, such as deletions, insertions and mutations that may involve one or more bases in selected genes. Rather than isolating and sequencing the target gene, it is sufficient to identify only the SNP involved. Additionally, SNP's and point mutations can be used in forensic medicine to positively identify individuals. While other genetic markers are available, the large number of SNP's and point mutations and their extensive distribution in the chromosomes, make the SNP's an attractive target. Also, by determining a plurality of SNP's associated with a specific phenotype, one may use the SNP pattern as an indication of the phenotype, rather than requiring a determination of the genes associated with the phenotype.

The need to identify a large number of bases distributed over potentially centimorgans of DNA offers a major challenge. Any method should be accurate, reasonably economical in limiting the amount of reagents required and providing for a single assay that allows for differentiation of the different SNP or point mutation. Many methods have been described for the detection of these genetic polymorphisms. For example, U.S. Pat. No. 6,110,709 describes a method for detecting the presence or absence of an SNP in a nucleic acid molecule by first amplifying the nucleic acid of interest, followed by restriction analysis and immobilizing the amplified product to a binding element on a solid support. Patent Publication WO9302212 describes another method for amplification and sequencing of nucleic acid in which dideoxy nucleotides are used to create amplified products of varying lengths. The varying length products are then separated and visualized by gel electrophoresis. Patent Publication WO0020853 further describes a method of detecting single base changes using tightly controlled gel electrophoretic conditions to scan for conformational changes in the nucleic acid caused by sequence changes.

In order to screen a large number of different samples, there is a need for a method with improved efficiency. It is therefore an object of the present invention to provide a novel method for scoring single nucleotide polymorphism.

SUMMARY

The present invention relates to a method of identifying a target nucleotide, single nucleotide polymorphisms ("SNP") or point mutations in a nucleic acid molecule. This method utilizes single and double base extensions of oligonucleotide primers that are complementary to the nucleic acid molecule containing the SNP or point mutation. The predicted extension length of the oligonucleotide primers in the presence of a chain-terminating nucleotide (dideoxynucleoside triphosphate ("ddNTP")) and presence or absence of chain-extending nucleotide (e.g. deoxynucleoside triphosphate ("dNTP")) are compared with the experimental extension lengths to identify the SNP or point mutation. The predicted amounts of label from a labeled ddNTP incorporated on to the oligonucleotide primers can also be compared with the experimentally observed amounts of incorporation to identify the SNP or point mutation.

In one embodiment of the present invention an oligonucleotide primer is hybridized to a nucleic acid molecule such that the oligonucleotide primer is complementary to the sequence of the nucleic acid molecule that is immediately adjacent to the known SNP or point mutation site on the 3' side. The oligonucleotide and nucleic acid molecule are hybridized together and form a hybridized-nucleic acid structure. The oligonucleotide primer can then be extended under polymerization conditions that will yield a zero, one or two base extension of the oligonucleotide primer with the complementary nucleic acid bases of the nucleic acid molecule that contains the SNP or point mutation acting as template for the extension. For example, adding a dideoxynucleoside triphosphate ("ddNTP") species to a polymerization reaction mixture will assure that any extension reaction of the oligonucleotide primer will terminate when the base complementary to the ddNTP in the nucleic acid molecule template is reached. In the present invention, the same ddNTP that is complementary to the nucleotide that is directly adjacent to the SNP or point mutation site on the 5' side is used in each polymerization reaction mixture. This allows the polymerization reaction to extend the primer by no more than one nucleotide past the 5' side of the SNP. Three reaction containers are used that all contain the same ddNTP species. To each reaction container, a deoxynucleoside triphosphate ("dNTP") species is added. Each of the three separate reaction containers contains a different dNTP species, and the nucleoside base of the dNTP in each reaction container is different from the nucleoside base of the ddNTP also present in the reaction container. The reaction containers are incubated in the presence of a polymerase reaction mixture for the purpose of extending the 3' hydroxy terminus of the oligonucleotide primer to form an extended-oligonucleotide primer. The length of the extended-oligonucleotide primer is then determined and compared in the three reaction tubes. The identity of the SNP or point mutation within a haploid template nucleic acid, a diploid template nucleic acid that is homozygous with respect to the SNP or point mutation, or a diploid template nucleic acid that is heterozygous with respect to the SNP or point mutation, can then be determined by utilizing a table of predicted lengths of the extended-oligonucleotide primers in each of the reaction tubes. It can also be determined by utilizing a table of predicted amounts of incorporation of label from a labeled ddNTP on to the primers in the different reaction tubes.

Another embodiment of the invention utilizes the method described above to detect SNP or point mutations in a solid-phase mode. Such an application in solid phase would allow mass genetic screening to occur on a surface such as a DNA chip. For example, oligonucleotide primers of DNA, RNA, or peptide nucleic acid ("PNA") with sequences complementary to a known sequence in a nucleic acid molecule on the 3' side of an SNP or point mutation can be coated on to a solid surface (e.g. glass, metal, plastic, nylon, beads or any other suitable matrices). The target nucleic acid molecule in the form of a PCR product can then be hybridized to the immobilized-oligonucleotide primer on the solid surface and serve as a template for extension of the primer. As similarly described above, the addition of an appropriate dNTP and ddNTP will extend the immobilized-oligonucleotide primers by zero, one or two bases. In the case of labeled ddNTP's a positive extension will yield a detectable labeled oligonucleotide primer. By employing experimental conditions under which the amount of label from labeled ddNTP incorporated into primer is proportional to the amount of template nucleic acid containing the SNP or point mutation, the amount of the template nucleic acid containing a particular SNP or point mutation allele can be estimated. Unlabelled oligonucleotide primers indicate the absence of any base extension. On this basis the presence or absence of a known SNP or point mutation within a haploid, homozygous diploid, or heterozygous diploid template nucleic acid can then be determined by utilizing a table of predicted amounts of label incorporation from a labeled ddNTP on to the oligonucleotide primers in reaction mixtures containing different dNTP's.

The table for predicting the identity of a single nucleotide polymorphism ("SNP") comprises column-heading, a row-heading and predicted lengths or amounts of label incorporation for an oligonucleotide primer. The column heading on the table representation represents the reaction condition suitable for extending an oligonucleotide primer to zero, one, or two, nucleotide bases longer than the oligonucleotide primer to form the extended-oligonucleotide primer. The row-heading on the table represents a nucleic acid sequence with potential permutations of the SNP, and the predicted lengths of extended-oligonucleotide primers are listed at the intersection point of the column-heading and the row-heading. By comparing the predicted length of the extended-oligonucleotide primer or predicted amount of label incorporation into the primer with an actual length of the extended-oligonucleotide primer or amount of label incorporation into the primer, one can use the table to distinctly indicate the identity of the SNP in the a haploid or diploid nucleic acid molecule.

BRIEF DESCRIPTION OF DRAWINGS

FIG. 2 shows a table that can be utilized to determine the identity of an SNP in a haploid target nucleotide by chain length analysis of the oligonucleotide primer extension in the reaction shown in FIG. 1, wherein the column-headings indicate a representation for a reaction condition suitable for extending an oligonucleotide primer; the row-headings show a representation of a nucleic acid sequence with potential permutations of the SNP; and the predicted length of an extended-oligonucleotide primer is listed at an intersection point of the column-heading and the row-heading, as shown in each box;

FIG. 3 shows a table that can be utilized to determine the identity of an SNP in a diploid target nucleotide by chain length analysis of the oligonucleotide primer extension in the reaction shown in FIG. 1, wherein the column-headings indicate a representation for a reaction condition suitable for extending an oligonucleotide primer; the row-headings show a representation of a nucleic acid sequence with potential permutations of the target nucleotides in a homozygous or heterozygous SNP site; and the predicted length of an extended-oligonucleotide primer is listed at an intersection point of the column-heading and the row-heading, as shown in each box;

FIG. 4 shows a table that can be utilized to determine the identity of an SNP in a haploid target nucleotide by incorporation of a labeled (by an isotopic, fluorescent or enzyme label) chain terminator nucleotide in an oligonucleotide primer extension in the reaction shown in FIG. 1, without analysis of the actual length of the primer elongation; wherein 0=no label incorporation, 2x=label incorporation into primer as the result of primer chain extension; wherein the column-headings indicate a representation for a reaction condition suitable for extending an oligonucleotide primer; the row-headings show a representation of a nucleic acid sequence with potential permutations of the SNP; and the predicted amount of label incorporation of an extended-oligonucleotide primer is listed at an intersection point of the column-heading and the row-heading, as shown in each box;

FIG. 5 shows a table that can be utilized to determine the identity of an SNP in a diploid target nucleotide by incorporation of a labeled (by an isotopic, fluorescent, or enzyme label) chain terminator nucleotide in an oligonucleotide primer extension in the reaction shown in FIG. 1, without analysis of the actual length of the primer elongation; wherein 0=no label incorporation, 1x=half-amount label incorporation into primers as the result of primer chain extension copying from half of the template DNA (i.e. one SNP allele of the template DNA); 2x=full-amount label incorporation into primers as the result of primer chain extension copying from all of the template DNA (i.e. two SNP alleles of the template DNA); wherein the column-headings indicate a representation for a reaction condition suitable for extending an oligonucleotide primer; the row-headings show a representation of a nucleic acid sequence with potential permutations of the target nucleotides in a homozygous or heterozygous SNP site; and the predicted amount of label incorporation of an extended-oligonucleotide primer is listed at an intersection point of the column-heading and the row-heading, as shown in each box;

FIG. 6 and FIG. 7 show schematic drawings in one aspect of the present invention; a nucleic acid molecule having a 3' portion and a 5' portion is amplified using amplification oligonucleotide primers 1 and 2 to PCR amplify a selected portion of a nucleic acid molecule having a target nucleotide, or SNP interposed between the oligonucleotide primers 1 and 2; the amplified nucleic acid molecule is hybridized with a third complementary oligonucleotide primer having a 3' and 5' portion; the target nucleotide, or SNP is directly adjacent to the 3' hydroxyl moiety of the third oligonucleotide primer;

FIG. 8 shows a table that can be utilized to determine the identity of an SNP in a haploid target nucleotide by chain length analysis of the third oligonucleotide primer extension in the reaction shown in FIG. 7, wherein the column-headings indicate a representation for a reaction condition suitable for extending a third oligonucleotide primer; the row-headings show a representation of a nucleic acid sequence with potential permutations of the SNP; and the predicted length of an extended-oligonucleotide primer is listed at an intersection point of the column-heading and the row-heading, as shown in each box;

FIG. 9 shows a table that can be utilized to determine the identity of an SNP in a diploid target nucleotide by chain length analysis of the third oligonucleotide primer extension in the reaction shown in FIG. 7, wherein the column-headings indicate a representation for a reaction condition suitable for extending the third oligonucleotide primer; the row-headings show a representation of a nucleic acid sequence with potential permutations of the target nucleotides in a homozygous or heterozygous SNP site; and the predicted length of an extended-oligonucleotide primer is listed at an intersection point of the column-heading and the row-heading, as shown in each box;

FIG. 10 shows a table that can be utilized to determine the identity of an SNP in a haploid target nucleotide by incorporation of a labeled (e.g. an isotopic, fluorescent or enzyme label) chain terminator nucleotide in the third oligonucleotide primer extension in the reaction shown in FIG. 7, without analysis of the actual length of the primer elongation; wherein 0=no label incorporation, 2x=incorporation into primer as result of primer chain extension; wherein the column-headings indicate a representation for a reaction condition suitable for extending the third oligonucleotide primer; the row-headings show a representation of a nucleic acid sequence with potential permutations of the SNP; and the predicted amount of label incorporation of an extended-oligonucleotide primer is listed at an intersection point of the column-heading and the row-heading, as shown in each box;

FIG. 11 shows a table that can be utilized to determine the identity of an SNP in a diploid target nucleotide by incorporation of a labeled (by isotopic, fluorescence or enzyme label) chain terminator nucleotide in the third oligonucleotide primer extension in the reaction shown in FIG. 7, without analysis of the actual length of the primer elongation; wherein the column-headings indicate a representation for a reaction condition suitable for extending the third oligonucleotide primer; the row-headings show a representation of a nucleic acid sequence with potential permutations of the target nucleotides in a homozygous or heterozygous SNP site; and the predicted amount of isotope label incorporation of an extended-oligonucleotide primer is listed at an intersection point of the column-heading and the row-heading, as shown in each box; and 0=no label incorporation, 1x=half-amount label incorporation into primers as the result of primer chain extension copying from half of the template DNA (i.e. one SNP allele of the template DNA); 233 =full-amount label incorporation into primers as the result of primer chain extension copying from all of the template DNA (i.e. two SNP alleles of the template DNA).

FIG. 12 shows a table that can be utilized to determine the identity of an SNP in a target nucleotide in either haploid or diploid nucleic acid molecule, wherein the incorporation of a labeled (by an isotopic, fluorescent or enzyme label) chain terminator nucleotide is used in a double incubation method; a pre-incubation occurs under a first reaction condition and a main incubation occurs under a second reaction condition; identity of the SNP is determined without analysis of the actual length of the primer elongation; wherein the column-headings indicate a representation for a reaction condition suitable for extending an oligonucleotide primer; the row-headings show a representation of a nucleic acid sequence with potential permutations of the target nucleotides in a homozygous or heterozygous SNP site; and the predicted amount of label incorporation of an extended-oligonucleotide primer is listed at an intersection point of the column-heading and the row-heading, as shown in each box; and 0=no label incorporation, 1x=half-amount label incorporation into primers as the result of primer chain extension copying from half of the template DNA (i.e. one SNP allele of the template DNA); 2x=full-amount label incorporation into primers as the result of primer chain extension copying from all of the template DNA (i.e. two SNP alleles of the template DNA).

DETAILED DESCRIPTION OF PREFERRED EMBODIMENTS

Figure 1:
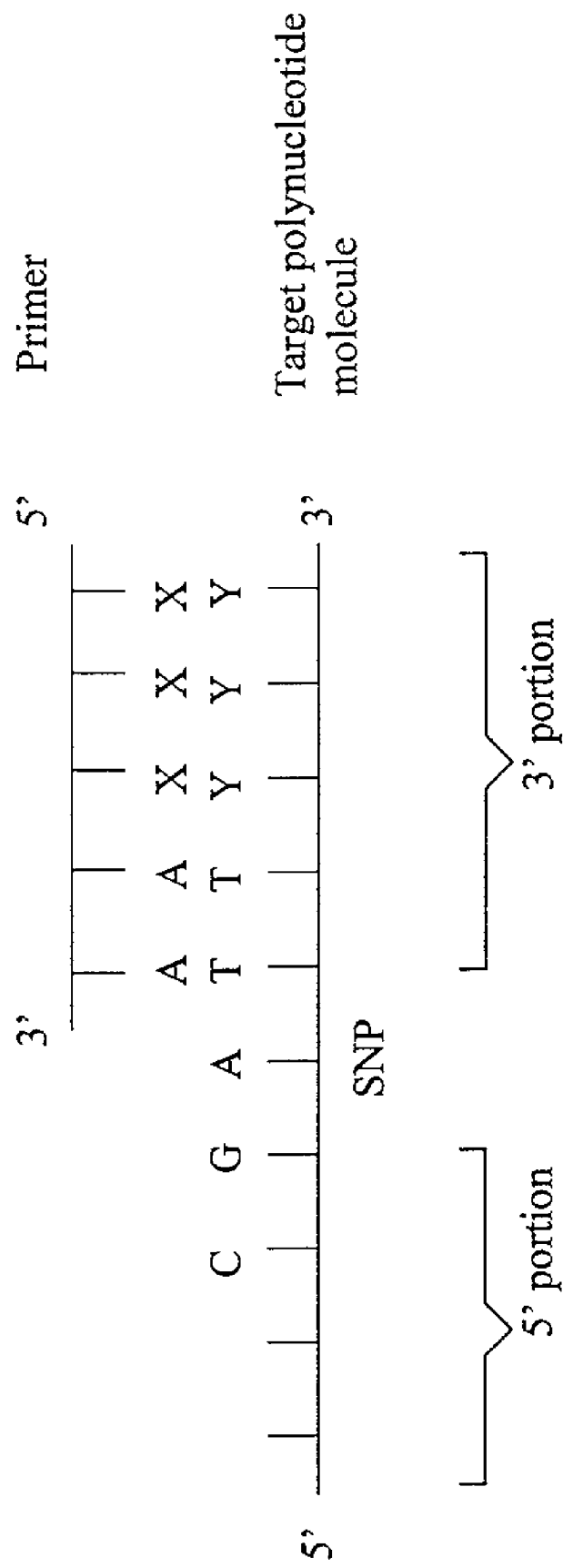
FIG. 1 shows a schematic drawing in one aspect of the present invention; a nucleic acid molecule having a 3' portion and a 5' portion is hybridized with a complementary oligonucleotide primer having a 3' and 5' portion; a target nucleotide, or SNP is directly adjacent to the 3' hydroxyl moiety of the oligonucleotide primer.

Terms:

It will be readily apparent to one skilled in the art that various substitutions and modifications may be made in the invention disclosed herein without departing from the scope and spirit of the invention.

The term "a" or "an" as used herein in the specification may mean one or more. As used herein in the claim(s), when used in conjunction with the word "comprising", the words "a" or "an" may mean one or more than one. As used herein "another" may mean at least a second or more.

The term "distinct chain-extending nucleotide" as used herein refers to adding a chain-extending nucleotide that has a single type of nitrogenous base group (e.g. A, or T, or G, or C, or a purine or a pyrimidine) in a single reaction container. Although a different reaction container may contain distinct chain-extending nucleotides (e.g. Tube 1-DATP, Tube 2-DTTP, Tube 3-dGTP), a single reaction container should not contain multiple types of chain-extending nucleotides with different nitrogenous base groups (e.g. dATP and dTTP in the same tube).

The term "hybridizing" as used herein refers to a method wherein the association of two complementary nucleic acid strands form double-stranded nucleic acid molecules, which can contain two DNA strands, two RNA strands, or one DNA and one RNA strand. The association of complementary strands occurs under a variety appropriate conditions (e.g. temperature, pH, salt concentration, etc.) that are well known in the art of molecular biology.

The term "3' hydroxyl moiety" as used herein refers to the hydroxyl group attached to the 3' carbon of a sugar end of a nucleic acid molecule, wherein 3' hydroxyl group forms an ester bond to the phosphate of another nucleotide eliminating a molecule of water in the process.

The term "target nucleotide" as used herein refers to a nucleotide of interest that is to be identified within a specific sequence or site in a nucleic acid molecule. The target nucleotide can also be referred to as the first pre-selected single nucleotide site in a nucleic acid molecule. Typically the target nucleotide is a single nucleotide polymorphism ("SNP") or point mutation.

The term "adjacent nucleotide" as used herein refers to a nucleotide in a nucleic acid molecule that is next to the target or the first pre-selected single nucleotide site that is to be identified. The adjacent nucleotide can also be referred to as the second pre-selected single nucleotide site in a nucleic acid molecule.

The term "aliquoting" as used herein refers to dividing a volume uniformly into parts.

The term "incubating" as used herein refers to a favorable environment for processing a reaction mixture. The favorable environment comprises temperature, enzyme concentration, salt concentration, pH conditions, or other favorable reaction conditions.

The term "polymerase reaction mixture" as used herein refers to favorable components for a polymerase enzyme to extend oligonucleotide primers.

The term "nucleotide" as used herein refers to any compound that consists of a nucleoside esterfied with a phosphate on its sugar moiety.

The term "nucleoside" as used herein refers to any glycosylamine that is a component of a nucleic acid and that comprises a nitrogenous base linked to a sugar.

The term "nucleotide base" as used herein refers to any nitrogenous base that is a constituent of a nucleoside or nucleotide in a nucleic acid, also synonymous with nucleoside base.

The present invention relates to a method of identifying the target nucleotide or genotyping single nucleotide polymorphisms ("SNP") and point mutations in a nucleic acid molecule. This method utilizes single and double base extensions of oligonucleotide primers that are complementary to the nucleic acid molecule containing the SNP or point mutation. The predicted extension length of the oligonucleotide primers in the presence of specific dideoxynucleoside triphosphate ("ddNTP") and deoxynucleoside triphosphate ("dNTP") molecules are compared with the experimental extension lengths to identify the SNP or point mutation. The same objective can also be accomplished by comparing the predicted and experimentally determined quantity of label incorporation from a labeled ddNTP into the oligonucleotide primers.

In one embodiment of the present invention an oligonucleotide primer is hybridized to a nucleic acid molecule such that a nucleotide complementary to the 3' terminus nucleotide of the oligonucleotide primer is directly adjacent on the 3' side to the known SNP or point mutation site. The oligonucleotide and nucleic acid molecule are hybridized together and form a hybridized-nucleic acid structure. The oligonucleotide primer can then be extended under polymerization conditions that will yield a zero, one-base or two-base extension of the oligonucleotide primer with the complementary nucleic acid bases of the nucleic acid molecule that contains the SNP or point mutation acting as template. For example, adding a dideoxynucleoside triphosphate ("ddNTP") species to a polymerization reaction mixture will assure that any extension reaction of the oligonucleotide primer will terminate when the complementary base to the ddNTP in the nucleic acid molecule template is reached. In the present invention, the same ddNTP that is complementary to the nucleotide site immediately 5' to the SNP or point mutation site is used in each polymerization reaction mixtures. This allows the polymerization reaction to extend the primer by at most one nucleotide past the SNP. Three reaction containers are used that all contain the same ddNTP species. To each reaction container, a deoxynucleoside triphosphate ("dNTP") species is added. Each of the three separate reaction containers contains a different dNTP species, and the nucleoside base of the dNTP in each reaction contains is different from the nucleoside base of the ddNTP already present in the reaction container. The reaction containers are incubated in the presence of a polymerase reaction mixture for the purpose of extending the 3' terminus of the oligonucleotide primer to form an extended-oligonucleotide primer. The length of the extended-oligonucleotide primer is then determined and compared in the three reaction tubes. The identity of the SNP's or point mutations in the nucleic acid molecule, either located within a haploid gene or a diploid gene can then be determined by utilizing a table of predicted lengths of the extended-oligonucleotide primers in each of the reaction tubes. It can also be determined by utilizing the table of the predicted amounts of label incorporation from a labeled ddNTP into the primers in each of the reaction tubes.

In one embodiment, a one-step elongation/termination reaction is followed by analysis of chain length or ddNTP incorporation to provide complete information on the SNP of interest. In this embodiment, a primer is furnished having a sequence complementary to the section of the a, target polynucleotide that is directly adjacent to the target nucleotide on the 3' side. The target nucleotide refers to the sequence location in which the SNP or point mutation to be screened is known to be located. A single ddNTP which is complementary to the nucleotide 5' adjacent to the SNP/point mutation is also provided in the reaction mixture. The ddNTP may be in a labeled or unlabeled form, depending on the method used for product analysis in the subsequent step. Also there may be present in the reaction mixture one dNTP with a base different from that in the ddNTP. In the case where the potential SNP/point mutation site and its 5' adjacent site in the target DNA share the same base identity, the incorporation of ddNTP could proceed without added dNTP.

The identity of the base at the potential SNP or point mutation site of the target DNA can be determined by checking for chain extension or labeled ddNTP incorporation after the elongation/termination reaction. Fully informative results can be obtained if different reaction mixtures are used, each containing a different dNTP. A dideoxy nucleotide-terminated polymerization that yields no primer extension or label incorporation suggests that the base of the target SNP nucleotide is not complementary to any ddNTP or dNTP present in the reaction mixture, while a one-base extension suggests that the SNP nucleotide is complementary to the ddNTP present. The production of oligonucleotide chains with two-base extension indicates that the target nucleotide contains a base that is complementary to the specific dNTP added to the reaction. In an example where the 5' nucleotide adjacent to the SNP site is G, if in the presence of ddCTP and dATP, but no other nucleotides, a two-base extension occurred in the elongation/termination reaction, the target polynucleotide at the potential SNP/point mutation site and its 5' adjacent site should read as T and G in the DNA, respectively. In one specific preferred embodiment, a set of three reactions is carried out in parallel, with or without also a control mixture devoid of dNTP. The three reaction mixtures all contain ddCTP, but differ from one another in the content of dNTP. For example, the first has dATP and may be designated A-Mix, the second has dTTP and may be designated T-Mix, the third has dGTP and may be designated G-Mix. The occurrence of incorporation of ddCTP in labeled or unlabelled form in any reaction mixture indicates that a base complementary to the dNTP or ddNTP present in the reaction mixture occupies the position of the potential SNP/point mutation site in the target DNA. If chain extension occurred in the control reaction in the absence of any added dNTP, the base of the target nucleotide must be complementary to that of the ddCTP in the reaction, and the target nucleotide is therefore G. In this case, the primer will be extended by only one base and not two.

In the case where two or three dNTPs are present in the reaction mixture along with the ddNTP, the base at the targeted SNP/point mutation site can be ambiguously identified to be complementary to the ddNTP or one of these dNTPs. This kind of experimental design can be useful for some special applications.

In another embodiment, some or all of the reactions may be performed in solid phase. A typical procedure for implementation in a solid-phase mode will include essentially the following steps: template amplification, quenching/purification, primer binding, primer extension, quenching/purification and detection, where each step can be varied and simplified under some conditions.

The principles described above are illustrated by way of the following examples:

EXAMPLE 1

A target polynucleotide molecule can be part of a haploid or homozygous diploid or heterozygous diploid human genomic DNA sequence. An example of such a target polynucleotide is shown in FIG. 1. The schematic drawing of FIG. 1 shows one aspect of the present invention; a nucleic acid molecule having a 3' portion, and a 5' portion is hybridized with a complementary oligonucleotide primer having a 3' and 5' portion; a target nucleotide, or SNP is directly adjacent to the 3' hydroxyl moiety of the oligonucleotide primer. The target polynucleotide in FIG. 1 shows an SNP with the nucleotide base A, (note—for ease of further description, the location of the SNP on the target polynucleotide is also referred to as the target nucleotide). Although the target nucleotide in FIG. 1 is A, it is known that among the human population, the other nucleotide bases C, G and T may also occur at this same site, but at different frequencies among the population. Furthermore, for the example target nucleotide, the nucleotide bases that flank the target nucleotide are known and do not vary in frequency as does the target nucleotide or SNP. Thus, for purposes of example, the starting material is a double stranded genomic DNA molecule with a SNP, which has been denoted as a target nucleotide (i.e. A), and the target nucleotide base A, may vary in frequency as to be G, T, or C in any given genomic DNA molecule, but the nucleotides that flank the target do not proportionally vary in frequency. The object will be for a user of this invention to identify the target nucleotide in a sample where the target nucleotide is unknown. The following paragraphs describe how the method according to the present invention may be applied to identify the target nucleotide at a specific location in an unknown DNA sample.

The first step in the process is the purification of the human genomic DNA and its separation from other contaminating material such as cell debris; such purification methods are well know to individuals with ordinary skill in the art and will not be discussed further here. After DNA purification, a primer, as indicated in FIG. 1, is provided for detection purpose according to the present invention. The primer contains a sequence that is complementary to the section of the target DNA that is directly 3' to the SNP. In this particular example, for simplicity only the two bases flanking each side of the SNP are shown. The other bases are indicated as Y's in the target DNA, and their complementary bases are indicated as X's in the primer. In this example, 2 bases TT are directly adjacent to the SNP on the 3' side. For ease of description, a 5-mer is used as an example for the primer, and contains the sequence 3'-AAXXX-5' as shown in FIG. 1, FIG. 2 and FIG. 3. The table of FIG. 2 shows how this table can be utilized to determine the identity of an SNP in a haploid target nucleotide by chain length analysis of the oligonucleotide primer extension in the reaction shown in FIG. 1, wherein the column-headings indicate a representation for a reaction condition suitable for extending an oligonucleotide primer; the row-headings show a representation of a nucleic acid sequence with potential permutations of the SNP; and the predicted length of an extended-oligonucleotide primer is listed at an intersection point of the column-heading and the row-heading, as shown in each box. The table shown in FIG. 3 can be utilized to determine the identity of an SNP in a diploid target nucleotide by chain length analysis of the oligonucleotide primer extension in the reaction shown in FIG. 1, wherein the column-headings indicate a representation for a reaction condition suitable for extending an oligonucleotide primer; the row-headings show a representation of a nucleic acid sequence with potential permutations of the target nucleotides in a homozygous or heterozygous SNP site; and the predicted length of an extended-oligonucleotide primer is listed at an intersection point of the column-heading and the row-heading, as shown in each box.

During the elongation/termination reaction, an appropriate polymerase enzyme is added to the reaction mix under suitable reaction conditions for the extension of the primer, such as, the presence of appropriate cofactors. Appropriate enzymes, factors and cofactors are well known by individuals with ordinary skill in the art. For example, reactions of DNA polymerase enzymes are typically carried out in the presence of $Mg^{++}$, which should be included in all reaction mixes. The components in three individual reaction mixtures, each containing a different dNTP, are shown in the top row of FIG. 2 and FIG. 3. For convenience, co-factors and reaction conditions are not shown. It is understood that the appropriate reaction conditions have to be provided for chain extension to occur. These are known in the art and may be obtained from standard laboratory manuals such as J. Sambrook et al. in Molecular Cloning: A Laboratory Manual, Cold Spring Harbor Laboratory Press, $2^{nd}$ edition, 1989. Since the nucleotide immediately adjacent to the SNP on the 5' side is known to the user, being a G in this instance, the dideoxy nucleotide that is elected is ddCTP, because C is complementary to G in base-pairing. In order to determine the base at the target location i.e. the SNP, three reaction mixes are used as shown in row 1 of FIG. 2. The three reaction mixes, namely A-Mix, T-Mix and G-Mix all contain the terminating nucleotide ddCTP, the primer and the target DNA. They also each contain one of the deoxyribonucleotides other than dCTP, namely dATP, dTTP on dGTP, respectively. Thus each of them contains a dNTP nucleotide with a unique base different from C.

A diploid organism contains two copies of most genes. Genotyping of a diploid organism in terms of any variant site involves the determination of whether the organism contains two copies of the reference allele (a reference-type homozygote), one copy each of the reference and variant allele (i.e., a heterozygote), or contains two copies of the variant allele (i.e., a variant-type homozygote). When conducting a genotyping analysis, the methods of the invention can be utilized to interrogate a single variant site. Most typically, SNP's consist of two allelic forms, i.e., the variant site includes one of two different nucleotides. The sample can contain nucleic acids representative of the two copies of the target nucleic acid of interest. The formation of two labeled extension products indicates that the sample is from a heterozygote.

The ability to use the methods of the invention to make rapid genotyping determinations provides a powerful tool in genetic analysis and ascertaining the susceptibility of an individual to a disease. Individuals that are homozygote for an allele associated with a particular disease are at higher risk of having the disease than a heterozygote or a homozygote for the other allele. The heterozygote, however, is a carrier of the allele associated with the disease. Such knowledge can be useful in prenatal and other types of medical and genetic counseling. Thus, if the target DNA is part of a haploid gene (e.g. located on an X or Y chromosome in a male), or part of a homozygous diploid gene, there is only one single sequence around the SNP, and rows 2–5 in the last column of FIG. 2 or FIG. 3 show the four possible bases that may be found at the SNP site, together with the two flanking bases on either side of the SNP site as shown in FIG. 1. The base at the SNP site is highlighted as boxed. The top row in FIG. 2 (as well as FIGS. 3, 4, 5, 8, 9, 10, 11 and FIG. 12 for reaction 2) also show a control-mix devoid of dNTP, which may be optionally included in the primer extension experiment.

As mentioned above, the base at the SNP site in the unknown haploid or homozygous diploid DNA sample is actually an A. Therefore, as shown in row 2 of FIG. 2, and FIG. 3, the T-Mix, where the presence of dTTP makes possible extension of the primer across the SNP site occupied by A, will yield a two-base extension of the primer terminated by ddCTP at the G residue 5' to the SNP, while no base extension is found in the A-Mix or G-Mix or Control Mix.

To fully illustrate the use of the present invention, the expected results of chain extension for each reaction mixture, when bases other than A are found at the target nucleotide site within a haploid or diploid homozygous gene, are shown in rows 3–5 of FIG. 2 and FIG. 3. In each row, the number of bases incorporated into the primer in each reaction mixture, and the actual sequence of the extended primer are shown. Thus in row 3, where the target nucleotide is a T, a 7-mer resulting from a two-base extension of the primer would be found in A-Mix, and no base extension is expected for T-Mix and G-Mix. If the target nucleotide contains a base C, a two-base extension (7-mer) would be expected in G-Mix while no reaction, with the primer remaining a 5-mer, would be expected in A-Mix and T-Mix. Finally, if the target nucleotide contains a base G, one base is expected to be added to the primer (i.e. to result in a 6-mer) in each of A-Mix, T-Mix and G-Mix as shown in row 5 of FIG. 2 and FIG. 3. Because the four different kinds of SNP nucleotides give rise to different predictions in the three reaction mixes in terms of occurrence of 0-base, 1-base or 2-base extensions of the primer, the pattern of primer extension in the three reaction mixes is sufficient to identify the nature of the SNP nucleotide. In fact, it is sufficient for this purpose just to examine the length of primer extension in any two of A-Mix, T-Mix and G-Mix.

When the target DNA containing the SNP nucleotide is part of a diploid gene heterozygous with respect to the SNP nucleotide, there will be two different sequences around the SNP, as indicated in the last column of rows 6–11 in FIG. 3. For these heterozygous genes, A-Mix in row 10, T-Mix in row 8 and G-Mix in row 11 each yields two kinds of chain extensions copied respectively from the two kinds of template sequences around the SNP. All other incubations in rows 6–11 yield simply no extension (0-base), a 1-base extension, or a 2-base extension. By determining which of these four kinds of outcomes, namely 0-base, 1-base, 2-base and [1-base plus 2-base] extensions, is observed in the three reaction mixes of A-Mix, T-Mix and G-Mix, the six heterozygous combinations of the SNP nucleotide, namely A/T in row 6, A/C in row 7, A/G in row 8, T/C in row 9, T/G in row 10 and C/G in row 11, as well as the four homozygous combinations in rows 2–5 all can be distinguished from one another. For example, none of the homozygous A/A, T/T, C/C and G/G predict a 2-base extension in more than one reaction mix; the heterozygous A/T, A/C and T/C, on the other hand, all predict a 2-base extension in two different reaction mixes. Again, for example, the A/T combination in row 6 predicts a 2-base extension in A-Mix and T-Mix. In contrast, the A/C combination in row 7 predicts a 2-base extension in T-Mix and G-Mix, whereas the T/C combination in row 9 predicts a 2-base extension in A-Mix and G-Mix. The other three heterozygous combinations of A/G, T/G and C/G, as well as homozygous G/G in row 5, all predict the finding of 1-base extension products in all of A-Mix, T-Mix, and G-Mix. However, only the T-Mix yields also a 2-base extension for the A/G combination in row 8, only the A-Mix yields a 2-base extension for the T/G combination in row 10, and only the G-Mix yields a 2-base extension for the C/G combination in row 11. In contrast, homozygous G/G does not yield a 2-base extension in A-Mix, T-Mix or G-Mix. Therefore the patterns of 0-base, 1-base, 2-base and [1-base plus 2-base] extensions in the three reaction mixes, or in fact in just any two of them, is sufficient to identify the heterozygous diploid SNP combination occurring in the target DNA.

From this example, it can be clearly seen that, by using a parallel set of three elongation/termination reactions, plus optionally a control reaction containing no added dNTP, the nature of the SNP nucleotide or nucleotides in a single nucleotide polymorphism can be readily identified for a haploid gene, a diploid gene homozygous with respect to the SNP nucleotide, or a diploid gene heterozygous with respect to the SNP nucleotide based on the lengths of primer extensions. The technique used for the chain length analysis of the extended primer may be any technique that is available in the art, including electrophoresis or mass spectroscopy. The length of the primer to be employed is dependent on many factors, including the base composition (which affects the melting temperature $T_m$) of the sequence, reaction temperature and hybridization stringency required, or other factors as determined by the user. For detection, the dideoxy nucleotide may be unlabelled, or chemically labeled with a radioactive isotope, with a fluorescent moiety or with an enzyme that can be used for colour-based analysis. For a radioactive isotope system, autoradiography may be performed after gel separation of the primer, its one-base extended product, and its two-base extended product. If capillary electrophoresis or mass spectroscopy is used, chain length may be determined without any labeling of the dideoxy nucleotide. Alternatively, fluorescence labeling may be used in conjunction with for instance gel or capillary electrophoresis.

If label measurement employing a labeled chain-terminating nucleotide is performed without carrying out chain length analysis to distinguish between one-base and two-base extensions, the result obtained would indicate the amount of labeled nucleotide incorporation into primer in a given reaction mixture, regardless of the actual length of the primer elongation. FIG. 4 shows a table that can be utilized to determine the identity of an SNP in a haploid target nucleotide by incorporation of a labeled chain terminator nucleotide in an oligonucleotide primer extension in the reaction shown in FIG. 1, without analysis of the actual length of the primer elongation; wherein 0=no label incorporation, 2x=label isotope incorporation into primer as the result of primer chain extension; wherein the column-headings indicate a representation for a reaction condition suitable for extending an oligonucleotide primer; the row-headings show a representation of a nucleic acid sequence with potential permutations of the SNP; and the predicted amount of label incorporation of an extended-oligonucleotide primer is listed at an intersection point of the column-heading and the row-heading, as shown in each box. From the result of the four possible haploid SNP genes shown in FIG. 4, it is clear that using the present invention, fully informative results may be obtained even without chain length analysis of primer elongation, because the four possible SNP nucleotides predict different "0" and "2x" incorporation patterns among the three reaction mixes of A-Mix, T-Mix and G-Mix. By using reaction conditions under which the quantity of template DNA is rate limiting, such that the amount of terminating nucleotide incorporation into primers varies with the quantity of template DNA, it becomes possible to distinguish between primer extension from a half, or haploid, set of templates (1x) and primer extension from a full, or diploid, set of templates (2x). Under these conditions, the results for the ten possible diploid SNP genes are shown in FIG. 5. The table shown in FIG. 5 can be utilized to determine the identity of an SNP in a diploid target nucleotide by incorporation of a chemically labeled chain terminator nucleotide in an oligonucleotide primer extension in the reaction shown in FIG. 1, without analysis of the actual length of the primer elongation; wherein 0=no label incorporation, 1x=half-amount label incorporation into primers as the result of primer chain extension copying from half of the template DNA (i.e. one SNP allele of the template DNA); 2x=full-amount label incorporation into primers as the result of primer chain extension copying from all of the template DNA (i.e. two SNP alleles of the template DNA); and wherein the column-headings indicate a representation for a reaction condition suitable for extending an oligonucleotide primer; the row-headings show a representation of a nucleic acid sequence with potential permutations of the target nucleotides in a homozygous or heterozygous SNP site; and the predicted amount of isotope label incorporation of an extended-oligonucleotide primer is listed at an intersection point of the column-heading and the row-heading, as shown in each box. Again, all ten SNP combinations, four of them homozygous and six heterozygous, can be completely distinguished from one another, because the ten SNP combinations predict ten different "0", "1x", "2x" incorporation patterns among the three reaction mixes.

To ensure that the experimental conditions employed for FIGS. 4 and 5 actually allow a clear and valid distinction between 0, 1x and 2x label incorporation, standard SNP-containing target polynucleotides predicting 0, 1x and 2x incorporation may be included in each experimental screening using the three reaction mixes alongside unknown SNP-containing DNA-samples. The SNP nucleotides in these standard target polynucleotides are already known from prior sequence determination. For example, standard A/A Polynucleotide is known to be diploid DNA containing a homozygous A/A SNP site, and standard G/G Polynucleotide is known to be diploid DNA containing a homozygous G/G SNP site. An aliquot of the A/A Polynucleotide brings about 0-base incorporation in A-Mix and G-Mix, but 2x incorporation in T-Mix. An aliquot of the standard G/G Polynucleotide in contrast brings about 2x incorporation in all these three mixes. When a half aliquot of standard A/A Polynucleotide and a half aliquot of G/G Polynucleotide are added together, the predicted outcomes, the same as those for an A/G heterozygous DNA, are 2x incorporation in T-Mix, but 1x incorporation in A-Mix and G-Mix. The observation of such predicted 0, 1x and 2x outcomes is a necessary and sufficient indication that the experimental conditions employed are adequate for the distinction between 0, 1x and 2x incorporation, so that conclusions drawn from FIG. 4 and FIG. 5 are valid.

The results in FIGS. 4 and 5 make clear that the amount of incorporation of labeled terminating nucleotide into the primer in the three reaction mixes can identify the SNP nucleotide or nucleotides in either a haploid or a diploid target polynucleotide, without chain length determination of whether the primer extensions within a reaction mix is in fact a 1-base or 2-base or [1-base plus 2-base] extension. These results are complementary to those shown in FIGS. 2 and 3. It is possible, for example, to confirm an SNP nucleotide identification obtained from FIG. 4 or 5 by repeating the identification based on FIG. 2 or 3, or vice versa.

EXAMPLE 2

Figure 6:
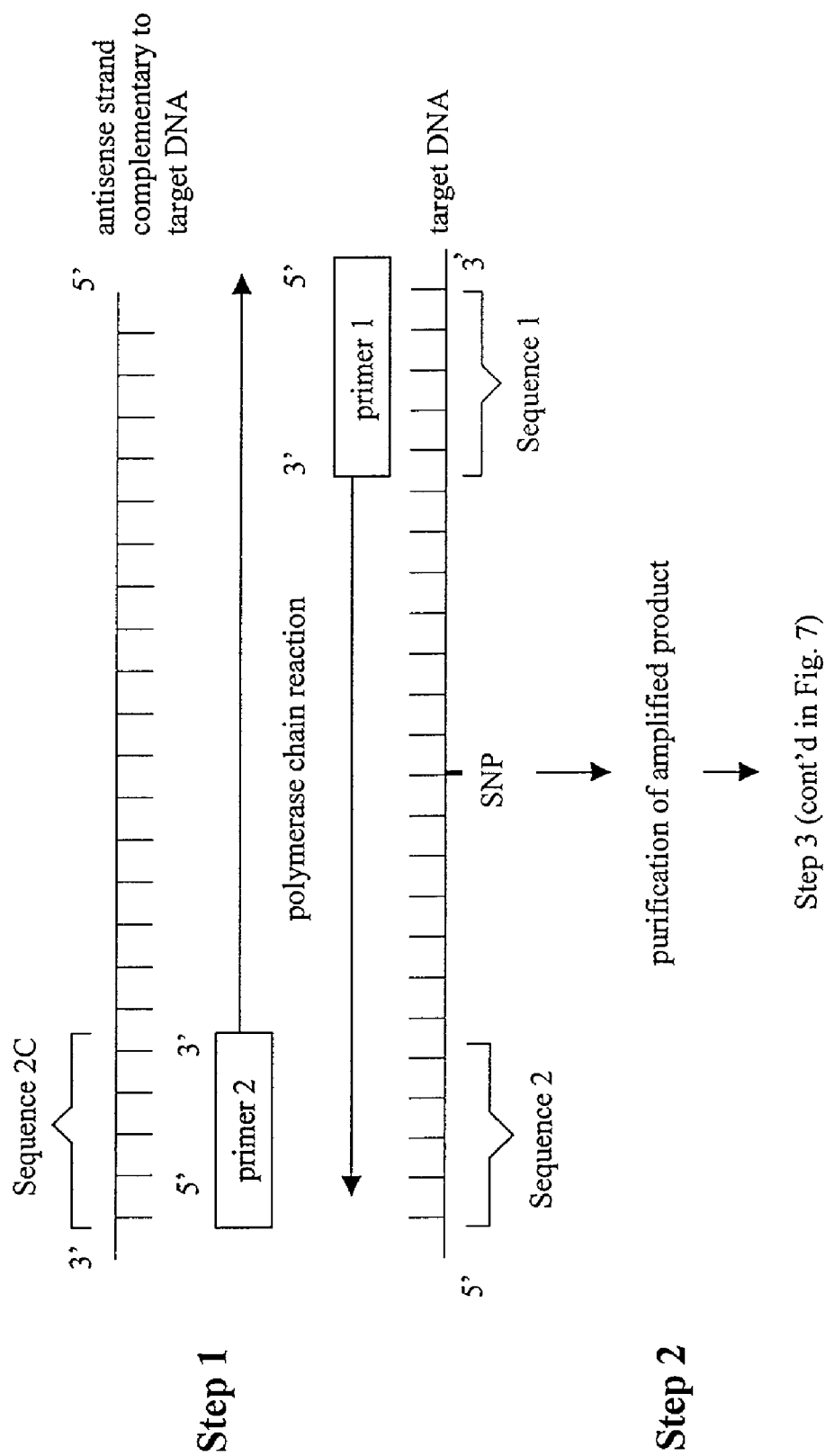

Example 2 is similar to Example 1 except that an amplification reaction is used before the elongation/termination reaction for the SNP determination. In this example, a very small quantity of target double stranded genomic DNA is isolated from a subject, and a polymerase chain reaction ("PCR") amplification step is first used to amplify the DNA sample. In this case, two primers are first used for the PCR reaction after genomic DNA purification, referred to as primer 1 and primer 2. FIG. 6 and FIG. 7 show schematic drawings in one aspect of the present invention; a nucleic acid molecule having a 3' portion and a 5' portion is amplified using amplification oligonucleotide primers 1 and 2 to PCR amplify a selected portion of a nucleic acid molecule having a target nucleotide, or SNP interposed between the oligonucleotide primers 1 and 2; the amplified nucleic acid molecule is hybridized with a third complementary oligonucleotide primer having a 3' portion and a 5' portion; a target nucleotide, or SNP, on the amplified target DNA is directly adjacent on the 3' side to the nucleotide of the 3' hydroxyl terminus of the third oligonucleotide primer. As shown in FIG. 6, primers 1 and 2 are complementary to Sequence 1 and Sequence 2C on a target DNA and its antisense strand respectively.

Sequence 1 is 3' downstream of the target SNP nucleotide. Sequence 2C is located on the complementary nucleic acid strand. Sequence 2, identical to primer 2, is complementary to Sequence 2C and located 5' upstream of the SNP. For ease of description, the relative positions of the primers are described in relation to only one strand (the target DNA) of the double-stranded nucleic acid (i.e. in relation to Sequence 1 and Sequence 2). It is understood that whenever the PCR reaction is required to amplify the signal, the two primers will be complementary to opposing strands of the double-stranded nucleic acid.

After PCR amplification under appropriate conditions known to the person of ordinary skill in the art, the amplification product is purified from the unreacted primers 1 and 2 as shown in step 2 of FIG. 6, using conventional methods such as size exclusion chromatography. The amplified product also may be freed of amplification primers and dNTPs by digestion with Exonuclease I (ExoI) and shrimp alkaline phosphatase.

During the elongation/termination reaction (shown in Step 3 of FIG. 7), the amplification product, also referred to as the amplified target DNA, containing the SNP of interest is hybridized with primer 3. Primer 3 is complementary to the 3' sequence (referred to as Sequence 3) directly adjacent to the SNP target nucleotide. For ease of description, only two bases (TT) directly adjacent to the SNP on the 3' side are shown in Sequence 3. The other bases are only indicated as Y's. The Xs shown in primer 3 are bases that are complementary to the corresponding Y's. In this example, the base directly adjacent to the target SNP on the 5' side is a C. Therefore, the dideoxy nucleotide that should be used for chain termination is ddGTP. Also in this example, the base at the target nucleotide location is an A. The reaction mixtures that are required to give completely informative results include a set of three parallel reactions. These three reaction mixtures are shown as A-Mix, T-Mix and C-Mix in FIG. 8 for a haploid target DNA. FIG. 8 shows a table that can be utilized to determine the identity of an SNP in a haploid target nucleotide by chain length analysis of the third oligonucleotide primer extension in the reaction shown in FIG. 7, wherein the column-headings indicate a representation for a reaction condition suitable for extending a third oligonucleotide primer; the row-headings show a representation of a nucleic acid sequence with potential permutations of the SNP; and the predicted length of an extended-oligonucleotide primer is listed at an intersection point of the column-heading and the row-heading, as shown in each box. The elongation/termination reactions are comparable to those described in Example One. Column 3 shows the elongation/termination reaction that would occur in T-Mix in the presence of ddGTP and dTTP. Since the target nucleotide is an A, dTTP would be added to the 3' end of primer 3 followed by the addition of ddGTP. Upon the addition of this dideoxy nucleotide, chain termination would occur and a 2-base extension is the result in this reaction mixture. By radioactively labeling the dideoxy nucleotide ddGTP with $^{32}$p, for example, the incorporation of the radioactive nucleotide would light up the two-base extended primer, which therefore can be detected after separation from the un-extended primer by gel electrophoresis and autoradiography.

To further illustrate how the present invention can be used to analyze the haploid target DNA sequences with different SNP bases, FIG. 8 shows the expected results for the set of three reaction mixes, namely A-Mix, T-Mix and C-Mix, each containing a dNTP nucleotide having a base different from that in the dideoxy nucleotide used in the reaction. This analysis is comparable to that shown in FIG. 2. The SNP base together with the flanking regions on either side in the haploid target DNA is shown in the rightmost column. The expected primer extensions to be found within the four reaction mixtures, namely A-Mix, T-Mix and C-Mix, plus a Control-Mix that may be included optionally, along with the sequences of the extended primer, are indicated in the space below each reaction mixture. Briefly, a two-base extension in the T-Mix containing dTTP would indicate that the target nucleotide is an A, while a two-base extension in C-Mix containing dCTP would indicate that the SNP nucleotide is a G. If a two-base extension is found in A-Mix containing dATP, then the target nucleotide is a T. If a one-base extension is found in all the reaction mixtures, then the target nucleotide is a C.

Alternatively, the amount of incorporation of labeled ddGTP into the primer can provide a measure of the number of extended primer chains in a particular reaction mixture, without using chain length analysis to distinguish between one-base and two-base extensions. The expected results are shown in FIG. 10 for the haploid target polynucleotide, and are comparable to those found in FIG. 4. They are sufficient for identifying the nature of the SNP nucleotide in the haploid target polynucleotide, because different SNP nucleotides predict different "0" and "2x" incorporation patterns among the different reaction mixtures, with or without inclusion of a Control-Mix.

When the target polynucleotide containing the SNP site is part of a diploid DNA sequence rather than haploid DNA sequence, the SNP site may occur in either homozygous form where the two SNP nucleotides occurring in the DNA are the same, or heterozygous form where the two SNP nucleotides are different. The pattern of extended primer chains synthesized in the A-Mix, T-Mix and C-Mix are predicted to be all different for the ten diploid SNP combinations, four of them homozygous and six of them heterozygous, in terms of the patterns of 0-base, 1-base, 2-base, and [1-base plus 2-base] extensions (FIG. 9). The table in FIG. 9 can be utilized to determine the identity of an SNP in a diploid target nucleotide by chain length analysis of the third oligonucleotide primer extension in the reaction shown in FIG. 7, wherein the column-headings indicate a representation for a reaction condition suitable for extending the third oligonucleotide primer; the row-headings show a representation of a nucleic acid sequence with potential permutations of the target nucleotides in a homozygous or heterozygous SNP site; and the predicted length of an extended-oligonucleotide primer is listed at an intersection point of the column-heading and the row-heading, as shown in each box. Likewise, when the amount of labelled terminator dideoxy nucleotide incorporation is determined, the patterns of "0", "1x" and "2x" incorporation are predicted to be all different for the ten diploid SNP combinations (FIG. 11).

Therefore, based on the results shown in FIG. 8, FIG. 9, FIG. 10 and FIG. 11, all four haploid SNP and all ten diploid SNP combinations can be distinguished from one another based on either chain-length analysis of the extended primers or determination of the amount of labeled dideoxy nucleotide incorporation by comparing the outcomes in three reaction mixtures each containing a different dNTP. A control mixture containing no added dNTP may also be included optionally for confirmatory purpose.

EXAMPLE 3

Example 3 is similar to Example 2 except that the 5' end of primer 3 is immobilized on to a solid surface. After PCR amplification similar to the one described in Example Two, the reaction mixture is quenched with shrimp alkaline phosphatase and ExoI, or purified by gel electrophoresis, to remove dNTPs and amplification primers. The amplified target DNA is then denatured and annealed with the immobilized primer 3. Multiple samples may be set up with an array of identical or different immobilized primers.

The elongation/termination reaction is initiated by adding the appropriate dideoxy-nucleotide to an extension mixture, with or without the inclusion of an extender dNTP nucleotide. In this case (FIG. 7), since the base directly adjacent to the SNP on the 5' side is a C, ddGTP is therefore always provided in the reaction mixes as the terminating nucleotide. In order for the reaction to be fully informative no matter which of the four possible nucleotides occurs at the SNP site within either a haploid or a diploid target DNA, extension reactions may be performed each using a different combination of nucleotides. The extension reaction mixture contains the polymerase reagents, immobilized primer 3, target polynucleotide, chain terminator ddGTP, and a chain extender (dNTP). The predicted patterns of primer chain extension and of the amount of chain terminator incorporation on to the immobilized primer are exactly the same as the predictions for the non-immobilized primer, as described in FIGS. 8, 9, 10 and 11.

With immobilized primers, it would be more difficult to analyze and distinguish between 1-base extensions and 2-base extensions. Therefore the predictions of FIGS. 10 and 11 could be more easily applied than those of FIGS. 8 and 9. However, immobilized primers offer the advantage of facilitating successive incubations of the same primer with different reaction mixtures. This advantage makes possible the Double-Incubation procedure indicated in FIG. 12.

In applying this Double Incubation method to for example primer 3 in FIG. 7, one portion of a target DNA is annealed to the immobilized primer 3 in Reaction 1, and thereupon treated with polymerase and labelled terminator nucleotide ddGTP, without any dNTP. In FIG. 7, the SNP site shown is A. Under these conditions, there will be no incorporation of label from ddGTP on to the immobilized primer. Similarly, there also will be no label incorporation if the SNP nucleotide is T or G. On the other hand, if the SNP nucleotide is C, label incorporation from labelled ddGTP will occur, signalling that the SNP nucleotide is in fact C.

To reveal the presence of SNP nucleotides other than C, Reaction 2 is performed. To do so, another portion of the target polynucleotide is annealed to a separate portion of immobilized primer from that used in Reaction 1, and subjected to Pre-incubation with polymerase and unlabelled ddGTP. After allowing time for primer extension to occur on any target polynucleotide with an SNP consisting of C, the primer-target polynucleotide hybrid is washed free of polymerase and the unlabelled ddGTP. Afterwards, polymerase is once again added in the Main Incubation together with labeled ddGTP plus dATP, dTTP or dCTP to form an A-Mix, T-Mix or C-Mix respectively.

Under the conditions of Reaction-2, during Pre-incubation any SNP site occupied by C would have caused primer extension incorporating the unlabelled form of the terminating nucleotide ddGTP. On an SNP site occupied by A, T or G, on the other hand, there will be no primer extension in the presence of unlabelled GTP alone during Pre-incubation. Instead, there will be a 2-base extension with label incorporation from labeled ddGTP when the primer is subsequently incubated in the Main Incubation with labeled ddGTP and dTTP in the T-Mix for an SNP site of A, with labeled ddGTP and dATP in the A-Mix for an SNP site of T, or with labeled ddGTP and dCTP in the C-Mix for an SNP site of G.

The results of Reaction-1 and Main Incubation of Reaction-2 for A-Mix, T-Mix and C-Mix, all containing a labeled ddGTP, are sufficient for distinguishing between all four possible haploid SNP, and all ten possible diploid SNP (FIG. 12).

To distinguish between all four haploid SNP's, or between all ten diploid SNP's on the basis of FIG. 12, it is only necessary to differentiate experimentally between "0" and "1x" or between "0" and "2x" label incorporation. There is no need to distinguish between "1x" and "2x" label incorporation, which in the case of immobilized primers might be more difficult to ascertain. For example, the T/T diploid SNP in FIG. 12 predicts 0-incorporation in T-Mix and C-Mix in Main Incubation of Reaction-2, and 2x-incorporation in A-Mix. By comparison, the T/C diploid SNP also predicts 0-incorporation in T-Mix and C-Mix, but 1x-incorporation in A-Mix. However, there is no need to distinguish between T/T and T/C solely relying on an experimental differentiation in A-Mix in Main Incubation of Reaction-2 between the "2x" incorporation predicted by T/T and the "1x" incorporation predicted by T/C. Instead, it would be straightforward to differentiate between the "0" incorporation predicted by T/T and the "1x" incorporation predicted by T/C in Reaction-1. Such differentiation can be achieved, for instance, by employing a fluorescence-labelled chain terminator ddGTP, and monitoring the incorporation of fluorescence label on to the immobilized primer by means of a detector sensitive to the label, e.g. a fluorescence array scanner or reader. The optional inclusion of a Control-Mix in the analysis in FIG. 12 will provide extra confirmation.

It is clear from the description above that many reaction combinations may be designed based on the present invention. Thus, while the present invention is specifically described with reference to the afore-mentioned examples, it should be understood that these examples are for illustration only and should not be taken as limitation on the invention. It is contemplated that many changes and modifications may be made by one of ordinary skill in the art without departing from the spirit and the scope of the invention described. The primers used in the examples are extremely short for ease of illustration. As discussed above, the length of the primers may vary according to the user's needs.

For example, although Example Two describes the use of PCR reaction as an amplification step, followed by nucleic acid purification to separate the primers from the amplified products, it should be understood that should primers 1 and 2 be designed in such a way as to be distinguishable from primer 3, then it becomes unnecessary even to have the purification step. For example, if primers 1 and 2 are of a length that is substantially longer than primer 3, even with a 2 base-extension of primer 3 in the subsequent Step 3 (FIG. 7), a technique that is capable of distinguishing between the three different primers and their dideoxynucleotide-terminated polymerase-extended products by size would be able to produce informative data regarding chain extension of primer 3 even in the presence of primers 1 and 2, without the purification step after DNA amplification. In general, if size detection is used to distinguish between the polymerase-extended products, then a primer 3 of less than 50 bases would be preferred, as most mass spectroscopic methods work well only with DNA fragments not much longer than 50 base pairs. If capillary electrophoresis is used as the separation method for analyzing the length of primer extension, a primer of less than 100 bases in length may be advantageous. Thus the optimal length of primer 3 to be employed depends on the method of size detection used and may be determined by the end user. As a non-limiting example, a primer for the chain elongation/termination reactions could be 15–55 bases in length.

It is thus clear that, although the primers used in Examples One and Two are very short simply for ease of illustration, primers of different lengths may employed. In the example shown in FIG. 6, although there are only 7 bases shown between Sequence 1 and the SNP site, and 6 bases between Sequence 2 and the SNP site, it should be understood that the position of Sequence 2 may be any distance 5' upstream, and Sequence 1 any distance 3' downstream, of the SNP site as long as the base directly adjacent to the SNP on the 5' side is also amplified, and the amplified product has sufficient length for primer 3 as shown in FIG. 7 to anneal to and for the polymerase to transcribe from during the subsequent elongation/termination reaction. Preferably there should be a minimum of 100 bases between Sequence 2 and the SNP, and more preferably more than 100 bases between them. Sequence 1 together with the intervening sequence between Sequence 1 and the SNP site in FIG. 6 preferably should be of a length comparable to primer 3.

The PCR reaction can be symmetrical, meaning that the two amplification primers are present at roughly equal molar concentrations, or it can be asymmetrical, in which one of the primers is added at 100 molar excess.

Also, as shown in Example One, if sufficient DNA can be obtained from the source material, it is possible to do the elongation/termination reaction without prior DNA amplification. Furthermore, if a sufficiently sensitive technique is used to detect the primers after dideoxy-nucleotide chain termination, it is contemplated that the reaction can be scored using a smaller amount of DNA without prior amplification. On the other hand, DNA purification may be rendered non-essential if specific amplification by PCR can be achieved using highly specific primers.

DNA and the use of dNTP and ddNTP are used in the aforementioned examples. It is clear that the polymerase may be DNA polymerase or any other nucleic acid extender that may be available to one in the art. The use of RNA polymerase with appropriate 3' deoxy-NTP or 2',3'dideoxy-NTP as terminating nucleotide might also follow the same principle. Different nucleic acid extenders may prefer different nucleotides for chain extension and chain termination. It is understood that the appropriate nucleotide co-factors and reaction conditions for use for chain extension would be provided, as well as an appropriate chain-terminating nucleotide for chain termination. Thus, the term extender nucleotide is used in the claims to refer to nucleotides that are used for chain extension including but not necessarily restricted to 2'-deoxyribonucleoside-5'-triphospates (dNTP).

Sometimes not all four bases are necessarily found in an SNP polymorphism. Thus, if a particular polymorphism consists of only two bases, it is possible that a reduced number of parallel reaction mixes may be required to provide a completely informative result.

For instance, if only the frequency of one specific base at an SNP site needs to be scored, e.g., the base G with a 5' adjacent C, a single reaction containing dCTP and ddGTP should in principle be sufficient to provide the required information. However, parallel reactions containing dATP plus ddGTP, dTTP plus ddGTP or ddGTP alone could be included for confirmation purposes. Alternatively, one of the reaction mixtures may be omitted from the elongation/termination reaction to save costs while retaining the capacity of the method to give fully informative results. For example, A-Mix in FIG. 4 may be omitted, relying only on T-Mix and G-Mix to completely distinguish between the four SNP nucleotides. In other instances, the only answer that is required may be a Yes or No answer regarding a particular base in a polymorphic site that is indicative of an important disease. In this case, a reduced number of parallel reaction mixes may again be employed to reduce the cost of the screening.

In the case of an immobilized probe, an array of, for example, 96 or 384 probes may be immobilized on to the, solid surface at individually addressed locations. Each extension reaction may be carried out in a single cycle of template-primer annealing and chain extension, or in multiple thermal cycles interspersed with thermal melting of the template-primer hybrid to increase sensitivity. For Reaction 2 in FIG. 12, however, the template-primer hybrid is not melted after the Pre-incubation step.

Post-extension treatment by shrimp alkaline phosphatase or calf intestinal alkaline phosphatase will remove unincorporated ddNTP's after each thermal cycle. Such treatment may be needed in cases, for instance, where incorporation of fluorescence labeled ddNTP is monitored by capillary electrophoresis, since left untreated the unincorporated fluorescent ddNTP's may overlap and interfere with the primer of interest. Removal of the 5' phosphoryl groups by phosphatase treatment alters the migration of the unincorporated fluorescent ddNTP's and thus may reduce interference. Such treatment may be performed just before the detection of extension products, and not needed for every thermal cycle.

It is also within the scope of the present invention to provide an SNP scoring method in which multiple probes are immobilized on to a single chip such that multiple SNP's representing different polymorphisms may be scored simultaneously for genetic material from the same individual or isolate, or different individuals or isolates.

From the foregoing description, it is clear that the present invention has many advantages:

The use of only one ddNTP rather than four as in single-base primer extension methods reduces the cost of labeled ddNTP's, which can be significant in large-scale and fluorescence-labeled tests. This feature also renders applicable detection methods that can accommodate only a single label, such as most radioactive or enzyme-linked color labels.

Because the detection of the incorporation of only one kind of chain-terminating nucleotide is required, the present invention based on analysis of up to two-base extension is more generally applicable than other single-base extension methods typically requiring four different kinds of labeled ddNTP's. Thus the two-base extension methods described herein can be performed on technology platforms not well suited for the simultaneous detection of multiple signals such as those emitted by different fluorescent labels. Such platforms include detection on a solid surface exemplified by as a 96-well plastic plate or a DNA chip, and also procedures entailing separation of un-extended and extended probes in solution phase, for example using high performance liquid chromatography or capillary electrophoresis. Reaction mixtures based on the present invention can be implemented readily in any of these environments.

Methods derived from this invention have the greatest potential for development into widely distributable genotyping kits on account of their simplicity in monitoring requirement as well as reduced costs in labeling with substances such as fluorescent dyes.

Two-base extension methods are also easily applied to the determination of SNP allele frequencies and association studies in pooled DNA's, which are more sensitive to quantitative errors. Since only one ddNTP is used in a two-base extension method, quantification of the incorporated ddNTP should be subject to less experimental variations than those arising from for example the use of up to four different fluorescent dyes with overlapping fluorescence spectra.

Since the reactions employing different dNTP contents are carried out separately, e.g., in separate tubes, two-base extension methods are less demanding on separation techniques. The separation of the incorporated nucleotide from only one kind of unincorporated ddNTP, rather than four kinds of unincorporated ddNTP as in the case of single-base extension methods, would be needed.

Where methods such as fluorescence anisotropy, or mass spectroscopy, may be employed for detection of primer extension, no separation might be needed prior to a one-step detection of the occurrence of chain extension. Fluorescence anisotropy might be readily analyzed for a single fluorescent label as called for by the present invention, for example, but becomes much less practicable when four different fluorescent labels require analysis as in the case of one-base extension methods.

Mass spectroscopy is an instrumental approach that allows for the mass measurement of molecules. By ionizing separating, and measuring molecular ions according to their mass-to-charge ratio (m/z), a mass spectrum can provide molecular weight or even structural information. Mass spectrometers have become pivotal for a wide range of applications in the analysis of inorganic, organic, and bio-organic chemicals. Further, mass spectrometry is being continually improved and significant advances in its application have become well know to the art of molecular biology.

What is claimed is:

1. A method for identifying a target nucleotide in a nucleic acid molecule having a 3' terminus, and a 5' terminus with the target nucleotide located between the 3' terminus and the 5' terminus of the nucleic acid molecule, the method comprising:
   (a) mixing an oligonucleotide primer with the nucleic acid molecule in a plurality of reaction containers, wherein the oligonucleotide primer having a free 3' hydroxyl moiety becomes hybridized to a complementary sequence on the nucleic acid molecule directly adjacent to the target nucleotide on the 3' side;
   (b) providing a corresponding chain-terminating nucleotide to each reaction container, wherein the corresponding chain-terminating nucleotide is complementary to an adjacent nucleotide that is directly next to the target nucleotide on the 5' side;
   (c) adding a distinct chain-extending nucleotide to each reaction container, wherein each reaction container has the same corresponding chain-terminating nucleotide but the distinct chain-extending nucleotide is different in each reaction container;
   (d) conducting a template dependant extension of the oligonucleotide primer by adding a polymerase reaction mixture to each of the reaction containers to give an extended primer;
   (e) detecting an incorporation of nucleotides into the extended primer, wherein the identity of the target nucleotide is determined from the extended primer size; wherein, only one corresponding chain-terminating nucleotide is present in any reaction container.

2. The method of claim 1, wherein the target nucleotide comprises a single nucleotide polymorphism ("SNP").

3. The method of claim 1, wherein the target nucleotide comprises a point mutation.

4. The method of claim 1, wherein the nucleic acid molecule comprises an isolated genomic deoxyribonucleic acid ("DNA") molecule.

5. The method of claim 1, wherein the nucleic acid molecule comprises a polymerase chain reaction "PCR" amplified DNA molecule.

6. The method of claim 1, wherein the oligonucleotide primer has a length in the range of about 15 to 55 nucleic acid residues.

7. The method of claim 1, wherein the oligonucleotide primer comprises a 5' portion attached to a solid surface.

8. The method of claim 1, wherein the chain-terminating nucleotide comprises a dideoxynucleoside triphosphate ("ddNTP") compound.

9. The method of claim 8, wherein the ddNTP is a natural compound or derivative thereof.

10. The method of claim 8, wherein the ddNTP comprises a dideoxynucleoside 5'-triphosphate.

11. The method of claim 1, wherein the chain-extending nucleotide comprises a deoxynucleoside triphosphate ("dNTP") compound.

12. The method of claim 11, wherein the dNTP is a natural compound or derivative thereof.

13. The method of claim 11, wherein the dNTP comprises 2'-deoxynucleoside 5'-triphosphate.

14. The method of claim 1, wherein the polymerase reaction mixture comprises a nucleic acid polymerase and a buffer.

15. The method of claim 1, wherein detecting the incorporation of nucleotides into the extended primer comprises determining a length of the extended primer.

16. The method of claim 15, wherein determining the length of the extended primer comprises an electrophoretic mobility analysis.

17. The method of claim 15, wherein determining the length of the extended primer comprises mass spectrometry analysis.

18. The method of claim 1, wherein the chain-terminating nucleotide comprises a chemically labeled nucleotide, the chemically labeled nucleotide being selected from a group consisting of a radioactive isotope, a fluorescent moiety, and an enzyme capable of generating a color signal.

19. The method of claim 18, wherein detecting the incorporation of chemically labeled nucleotide into the extended primer comprises determining a quantity of the chemically labeled nucleotide that has been incorporated into the extended primer.

20. The method of claim 1, wherein identifying the target nucleotide in the nucleic acid molecule comprises matching an experimentally determined length for the extended-primer with a table of a corresponding predicted length for the extended-primer.

21. The method of claim 1, wherein identifying the target nucleotide in the nucleic acid molecule comprises matching an experimentally determined incorporation of a chemically labeled nucleotide into the extended-primer with a table of a corresponding predicted incorporation of the chemically labeled nucleotide into the extended-primer, the chemically labeled nucleotide being selected from a group consisting of a radioactive isotope, a fluorescent moiety, and an enzyme capable of generating a color signal.

22. A method for identifying a target nucleotide in a nucleic acid molecule having a 3' terminus, and a 5' terminus with the target nucleotide located between the 3' terminus and the 5' terminus of the nucleic acid molecule, the method comprising:
   (a) immobilizing an oligonucleotide primer to a solid surface in a plurality of reaction containers, forming an immobilized-primer;
   (b) adding the nucleic acid molecule to the plurality of reaction containers carrying the immobilized-primer, wherein the immobilized-primer having a complementary 3' hydroxyl moiety becomes hybridized to a complementary sequence on the nucleic acid molecule directly adjacent on the 3' side to the target nucleotide;
   (c) providing a first corresponding chain-terminating nucleotide to each reaction container, wherein the first corresponding chain-terminating nucleotide is complementary to the target nucleotide;
   (d) pre-incubating the plurality of reaction containers in the presence of a pre-incubation-polymerase reaction mixture giving a pre-incubation-primer;
   (e) washing the plurality of reaction containers to remove the pre-incubation-polymerase reaction mixture and the first corresponding chain-terminating nucleotide;
   (f) providing a second corresponding chain-terminating nucleotide to each reaction container, wherein the second corresponding chain-terminating nucleotide is complementary to an adjacent nucleotide that is directly next to the 5' side of the target nucleotide;

(g) adding a distinct chain-extending nucleotide to each reaction container, wherein each reaction container has the same second corresponding chain terminating nucleotide but the distinct chain-extending nucleotide is different in each reaction container;

(h) conducting a template dependant extension of pre-incubation-primer by adding a polymerase reaction mixture to each of the reaction containers to extend the primer; and (i) detecting an incorporation of nucleotides into the extended primer, wherein the identity of the target nucleotide is determined from the extended primer size.

23. The method of claim 22, wherein the target nucleotide comprises a single nucleotide polymorphism ("SNP").

24. The method of claim 22, wherein the target nucleotide comprises a point mutation.

25. The method of claim 22, wherein the nucleic acid molecule comprises an isolated genomic deoxyribonucleic acid ("DNA") molecule.

26. The method of claim 22, wherein the nucleic acid molecule comprises a polymerase chain reaction "PCR" amplified DNA molecule.

27. The method of claim 22, wherein the immobilized-primer has a length in the range of about 15 to 55 nucleic acid residues.

28. The method of claim 22, wherein the first corresponding chain-terminating nucleotide comprises a dideoxynucleoside triphosphate ("ddNTP") compound.

29. The method of claim 28, wherein the ddNTP is a natural compound or derivative thereof.

30. The method of claim 28, wherein the ddNTP comprises a 2',3'-dideoxynucleoside 5'-triphosphate.

31. The method of claim 22, wherein the second corresponding chain-terminating nucleotide comprises a dideoxynucleoside triphosphate ("ddNTP") compound.

32. The method of claim 31, wherein the ddNTP is a natural compound or derivative thereof.

33. The method of claim 31, wherein the ddNTP comprises a 2',3'-dideoxynucleoside 5'-triphosphate.

34. The method of claim 22, wherein the chain-extending nucleotide comprises a deoxynucleoside triphosphate ("dNTP") compound.

35. The method of claim 34, wherein the dNTP is a natural compound or derivative thereof.

36. The method of claim 34, wherein the dNTP comprises 2'-deoxynucleoside 5'-triphosphate.

37. The method of claim 22, wherein the pre-incubation polymerase reaction mixture comprises a nucleic acid polymerase and a buffer.

38. The method of claim 22, wherein the polymerase reaction mixture comprises a nucleic acid polymerase and a buffer.

39. The method of claim 22, wherein detecting the incorporation of nucleotides into the extended primer comprises determining a length of the extended primer.

40. The method of claim 39, wherein determining the length of the extended primer comprises an electrophoretic mobility analysis.

41. The method of claim 39, wherein determining the length of the extended primer comprises mass spectrometry analysis.

42. The method of claim 22, wherein the first chain-terminating nucleotide comprises a chemically labeled nucleotide, the chemically labeled nucleotide being selected from a group consisting of a radioactive isotope, a fluorescent moiety, and an enzyme capable of generating a color signal.

43. The method of claim 22, wherein the second chain-terminating nucleotide comprises a chemically labeled nucleotide, the chemically labeled nucleotide being selected from a group consisting of a radioactive isotope, a fluorescent moiety, and an enzyme capable of generating a color signal.

44. The method of claim 43, wherein detecting the incorporation of nucleotides into the extended primer comprises determining a quantity of the labeled nucleotide that has been incorporated into the extended primer.

45. The method of claim 22, wherein the chain-extending nucleotide comprises a chemically labeled nucleotide, the chemically labeled nucleotide being selected from a group consisting of a radioactive isotope, a fluorescent moiety, and an enzyme capable of generating a color signal.

46. The method of claim 45, wherein detecting the incorporation of the nucleotides into the extended primer comprises determining a quantity of the chemically labeled nucleotide that has been incorporated into the extended primer.

47. The method of claim 22, wherein identifying the target nucleotide in the nucleic acid molecule comprises matching an experimentally determined length of the extended-primer with a table of corresponding predicted lengths for the extended-primer.

48. The method of claim 47, wherein the nucleic acid molecule has a haploid DNA sequence.

49. The method of claim 47, wherein the nucleic acid molecule has a diploid DNA sequence.

50. The method of claim 49, wherein the diploid DNA sequence is heterozygous.

51. The method of claim 49, wherein the diploid DNA sequence is homozygous.

52. The method of claim 1, wherein identifying the target nucleotide in the nucleic acid molecule comprises matching an experimentally determined incorporation of a chemically labeled nucleotide into the extended-primer with a table of a corresponding predicted incorporation of the chemically labeled nucleotide into the extended-primer.

53. The method of claim 52, wherein the chemically labeled nucleotide is selected from a group consisting of a radioactive isotope, a fluorescent moiety, and an enzyme capable of generating a color signal.

54. The method of claim 52, wherein the nucleic acid molecule has a haploid DNA sequence.

55. The method of claim 52, wherein the nucleic acid molecule has a diploid DNA sequence.

56. The method of claim 55, wherein the diploid DNA sequence is heterozygous.

57. The method of claim 55, wherein the diploid DNA sequence is homozygous.

58. A method for identifying a target nucleotide in a nucleic acid molecule having a 3' terminus, and a 5' terminus, with the target nucleotide being located between the 3' terminus and the 5' terminus of the nucleic acid molecule, the method comprising:

(a) reacting an oligonucleotide primer with the nucleic acid molecule in a solution to form a mixture, wherein the oligonucleotide primer having a complementary 3' hydroxyl moiety becomes hybridized to a sequence on the nucleic acid molecule directly adjacent on the 3' side to the target nucleotide;

(b) aliquoting a volume of the mixture into a first, a second, a third, and a control reaction container;

(c) providing a chain-terminating nucleotide to the first, the second, the third, and the control reaction containers, wherein the chain-terminating nucleotide is complementary to an adjacent nucleotide that is directly on the 5' side to the target nucleotide;

(d) adding a distinct chain-extending nucleotide to the first, the second and the third reaction containers, wherein the distinct chain-extending nucleotide comprises a nucleoside base that is different from the nucleoside base of the chain-terminating nucleotide;

(e) incubating the first, the second, the third, and the control reaction containers in the presence of a polymerase reaction mixture to form a null-, one-, or two-complementary base extension length to the 3' hydroxyl moiety of the oligonucleotide primer giving an incubated-primer;

(f) analyzing the null-, one-, or two-complementary base extension length of the incubated-primer in each of the first, the second, the third, and the control reaction containers; and (g) comparing the null-, one-, or two-complementary base extension length in the incubated-primer in each of the first, the second, the third, and the control reaction containers to identify the target nucleotide.

59. The method of claim 58, wherein the target nucleotide comprises a single nucleotide polymorphism ("SNP").

60. The method of claim 58, wherein the target nucleotide comprises a point mutation.

61. The method of claim 58, wherein the nucleic acid molecule comprises an isolated genomic deoxyribonucleic acid ("DNA") molecule.

62. The method of claim 58, wherein the nucleic acid molecule comprises a polymerase chain reaction "PGR" amplified DNA molecule.

63. The method of claim 58, wherein the oligonucleotide primer has a length in the range of about 15 to 55 nucleic acid residues.

64. The method of claim 58, wherein the oligonucleotide primer comprises a 5' end attached to a solid surface.

65. The method of claim 58, wherein the chain-terminating nucleotide comprises a dideoxynucleoside triphosphate ("ddNTP") compound.

66. The method of claim 65, wherein the ddNTP is a natural compound or derivative thereof.

67. The method of claim 65, wherein the ddNTP comprises a 2',3'-dideoxynucleoside 5'-triphosphate that is complementary to the adjacent nucleotide.

68. The method of claim 58, wherein the chain-extending nucleotide comprises a deoxynucleoside triphosphate ("dNTP") compound.

69. The method of claim 68, wherein the ddNTP is a natural compound or derivative thereof.

70. The method of claim 68, wherein the dNTP comprises 2'-deoxynucleoside 5'-triphosphate.

71. The method of claim 58, wherein the polymerase reaction mixture comprises a nucleic acid polymerase, and a buffer.

72. The method of claim 58, wherein analyzing the null-, one-, or two-complementary base extension length comprises determining a length of the incubated-primer.

73. The method of claim 72, wherein determining the length of the incubated-primer comprises an electrophoretic mobility analysis.

74. The method of claim 72, wherein determining the length of the incubated-primer comprises mass spectrometry analysis.

75. The method of claim 58, wherein the chain-terminating nucleotide comprises a chemically labeled nucleotide base.

76. The method of claim 75, wherein the chemically labeled nucleotide is selected from a group consisting of a radioactive isotope, a fluorescent moiety, and an enzyme capable of generating a color signal.

77. The method of claim 75, whereby analyzing the length of the null-, one-, or two complementary base extension length comprises determining a quantity of the chemically labeled nucleotides incorporated in the incubated-primer.

78. The method of claim 77, wherein the quantity of a labeled nucleotide incorporated in the incubated-primer comprises zero, one, or two chemically labeled nucleotide molecules.

79. The method of claim 58, wherein comparing the extension length of complementary bases added to the null-, one-, or two-complementary base extension length in the incubated-primer in the first, the second, the third, and the control reaction containers comprises utilizing a table of predicted lengths of the incubated-primer in the first, the second, the third, and control reaction containers, and comparing an actual nucleotide base pair extension in the null-, one-, or two-complementary base extension length in the incubated-primer to predicted nucleotide base pair extensions in the incubated-primer.

80. The method of claim 58, wherein the table of predicted lengths comprises a heading-row designating the first, the second, the third, control reaction containers and a haploid DNA sequence, and a heading-column listing a nucleotide sequence with four possible nucleotide base combinations of the target nucleotide in separate rows, and wherein a predicted number of nucleotide extensions of the null-, one-, or two-complementary base extension length in the incubated-primer are listed at an intersection point of the heading row and heading-column listing a nucleotide sequence for the four possible nucleotide bases.

81. The method of claim 58, wherein the table of predicted lengths comprises a heading-row designating the first, the second, the third, control reaction containers and a diploid DNA sequence, and a heading-column listing a nucleotide sequence with ten possible nucleotide base combinations of the target nucleotide in separate rows, and wherein a predicted number of nucleotide extensions of the null-, one-, or two-complementary base extension length in the incubated-primer are listed at an intersection point of the heading row and heading-column listing a nucleotide sequence for the ten possible nucleotide bases.

82. The method of claim 81, wherein the diploid DNA sequence is heterozygous.

83. The method of claim 81, wherein the diploid DNA sequence is homozygous.

* * * * *